United States Patent [19]

Hamada et al.

[11] Patent Number: 4,582,801

[45] Date of Patent: Apr. 15, 1986

[54] PROCESS FOR PRODUCING GLUTATHIONE

[75] Inventors: Shinichiro Hamada; Hisao Tanaka; Kuniaki Sakato, all of Hofu, Japan

[73] Assignee: Kyowa Hakko Kogyo Co., Ltd., Tokyo, Japan

[21] Appl. No.: 438,930

[22] Filed: Nov. 3, 1982

[30] Foreign Application Priority Data

Nov. 10, 1981 [JP] Japan ............................... 56-180192

[51] Int. Cl.⁴ .......................... C12N 1/16; C12R 1/85; C12R 1/865; C12P 21/02
[52] U.S. Cl. ..................................... 435/70; 435/255; 435/940; 435/942; 435/172.1
[58] Field of Search ................. 435/70, 172, 244, 245, 435/254, 255, 813, 940, 942

[56] References Cited

U.S. PATENT DOCUMENTS 4,081,326 3/1978 Hall ..................................... 435/201

FOREIGN PATENT DOCUMENTS 7005699 1/1982 Japan ..................................... 435/70
0028299 2/1983 Japan ..................................... 435/70

OTHER PUBLICATIONS

*American Type Culture Collection*, Catalogue of Strains I, 15th Edition, Jong, S. et al. editors, "Saccharomyces", Rockville, Md., pp. 480–493 (1982).
*Metabolic Inhibitors*, A Comprehensive Treatise, vol. II, Hochster, R. M. et al. editors, Academic Press, New York, pp. 414–436 (1963).
*Chemical Abstracts*, vol. 89, 1978, p. 453, Abstract No. 213599b, Miwa, N., "Production of Glutathione by Fermentation".
*Chemical Abstracts*, vol. 90, 1979, p. 390, Abstract No. 70580w, Murata, K. et al., "Continuous Production of Glutathione by Immobilized *Saccharomyces cerevisiae* Cells".
*Chemical Abstracts*, vol. 92, 1980, p. 458, Abstract No. 92731q, Chibata, I. et al., "Glutathione".

*Primary Examiner*—Blondel Hazel
*Assistant Examiner*—Robin Lyn Teskin
*Attorney, Agent, or Firm*—Antonelli, Terry & Wands

[57] ABSTRACT

A process for producing glutathione, involves cultivating a strain belonging to the genus Saccharomyces and having both an ability to produce glutathione and a resistance to 1,2,4-triazole or sodium azide in a culture medium accumulating glutathione in the microbial cells, harvesting the cells, and recovering the glutathione therefrom.

5 Claims, No Drawings

4,582,801

PROCESS FOR PRODUCING GLUTATHIONE

BACKGROUND OF THE INVENTION

1. Field of the Invention

The present invention relates to a process for producing glutathione. More specifically, it relates to a process which comprises cultivating a mutant strain of the genus Saccharomyces which is resistant to 1,2,4-triazole and/or sodium azide in a culture medium to accumulate large amounts of glutathione in the microbial cells and recovering the glutathione.

Glutathione, a tripeptide which takes part in an oxidation-reduction system in the living body, is useful as a medicine for strengthening liver functions, detoxification, and so forth.

2. Description of Prior Art

As industrial process for producing glutathione, synethetic processes, processes for extraction from yeasts, and so forth, have already been reported; however, the synthetic processes involve complicated steps for synthesizing the L-isomer having physiological activities, and the extraction from yeast cells, which affords only the L-isomer, has a defect that the yield is low.

As improved methods, there have been reported a process in which L-cysteine, a precursor of glutathione, alone or in combination with glutamic acid or glycine is added to the medium to increase the glutathione content of cells (Japanese Published Unexamined Patent Application Nos. 44488/1973, 92579/1973, 156994/1977 and 94089/1978), a process in which methionine or L-cystine is added to the medium to increase the glutathione content of cells (Japanese Published Unexamined Patent Application Nos. 22685/1973, 44487/1973, 139685/1976 and 156994/1977), and so forth. In addition, as methods employing improved yeasts, a process in which an L- or DL-ethionine-sensitive strain of *Candida utilis* is employed (Japanese Published Unexamined Patent Application No. 87296/1977), a process in which an ethionine-resistant strain of *Candida utilis* is employed (Japanese Published Unexamined Patent Application No. 125687/1977), and so forth, are known.

The production yields of such processes are comparatively low from a commercial application standpoint. Thus, a need exists for a process for producing glutathione in higher yields at low cost.

To this end, it has now been found that glutathione productivity of a glutathione-producing microorganism belonging to the genus Saccharomyces is greatly improved when such microorganism is endowed with a resistance to 1,2,4-triazole or sodium azide.

Heretofore, it was not recognized that the productivity of glutathione could be improved by endowing a glutathione-producing microorganism with either of such traits.

BRIEF SUMMARY OF THE INVENTION

As a result of improvement in yeasts, the present inventors have found that a strain of the genus Saccharomyces, resistant to 1,2,4-triazole or sodium azide, has an excellent ability to produce glutathione.

DETAILED DESCRIPTION OF THE INVENTION

In the process of the present invention, any glutathione-producing strain of the genus Saccharomyces which is resistant to 1,2,4-triazole or sodium azide can be used, and higher yields can be expected by further imparting to said strains properties such as resistance to other medicines, drug sensitivity, and nutritional requirement.

Examples of the strains are a 1,2,4-triazole-resistant strain *Saccharomyces cerevisiae* TRZ-6 (FERM BP-194), a sodium azide-resistant strain *Saccharomyces cerevisiae* N-33 (FERM BP-193), and a 1,2,4-triazole and sodium azide-resistant strain *Saccharomyces cerevisiae* TRZN-10 (FERM BP-195) which are derived from *Saccharomyces cerevisiae* ATCC 7754.

*Saccharomyces cerevisiae* TRZ-6, N-33 and TRZN-10 were deposited on Nov. 6, 1981 with the Fermentation Research Institute Agency of Industrial Science and Technology, Japan, and are available therefrom under the terms of the Budapest Treaty.

Methods for obtaining the foregoing TRZ-6 strain, N-33 strain, and TRZN-10 strain will be described below.

Method for obtaining a drug-resistant strain:

*Saccharomyces cerevisiae* ATCC 7754 was grown on a slant medium consisting of 1 g/dl glucose, 0.3 g/dl yeast extract, 0.3 g/dl malt extract, and 0.5 g/dl peptone at 30° C. for 24 hours to obtain a colony. After washing with physiological saline, the colony was suspended in a 0.05M Tris.malate buffer (pH 5.0) containing 200 $\mu$g/ml nitrosoguanidine in a concentration of about $10^8$ cells/ml, and then subjected to a mutagenic treatment at 30° C. for 30 minutes. The cells were washed once with physiological saline, and spread on each of the three kinds of minimum agar media of the following composition further containing 5 g/l 1,2,4-triazole, 50 mg/l sodium azide, and 5 g/l 1,2,4-triazole and 50 mg/l sodium azide, respectively. Each culturing was carried out at 30° C. for 3–7 days, and then TRZ-6, N-33 or TRZN-10 strain was selected from each of the formed colonies.

TABLE 1

| Composition Of The Minimum Agar Medium | |
|---|---|
| Glucose | 20 g/l |
| L-Asparagine | 2 g/l |
| $(NH_4)_2SO_4$ | 2 g/l |
| $KH_2PO_4$ | 1.5 g/l |
| $MgSO_4.7H_2O$ | 0.5 g/l |
| $CaCl_2.2H_2O$ | 0.33 g/l |
| $MnSO_4.nH_2O$ | 0.04 mg/l |
| $(NH_4)_6Mo_7O_{24}.4H_2O$ | 0.02 mg/l |
| $CuSO_4.5H_2O$ | 0.04 mg/l |
| $H_3BO_3$ | 0.6 mg/l |
| $ZnSO_4.7H_2O$ | 0.31 mg/l |
| Thiamine hydrochloride | 200 $\mu$g/l |
| Calcium pantothenate | 200 $\mu$g/l |
| Nicotinic acid | 200 $\mu$g/l |
| Pyridoxine hydrochloride | 200 $\mu$g/l |
| p-Aminobenzoic acid | 50 $\mu$g/l |
| Biotin | 2 $\mu$g/l |
| Agar | 20 g/l |
| pH 5.5 | |

The following experiments were carried out to confirm the drug resistance of the strains obtained.

The degree of growth of the drug resistant strain:

The parent strain *Saccharomyces cerevisiae* ATCC 7754 and the drug resistant strains derived therefrom were each inoculated in a concentration of $5\times10^6$ cells/ml into a minimum liquid medium (the medium in Table 1 lacking agar) containing the drugs each in concentrations shown in Tables 2 and 3. Culturing was carried out with shaking at 30° C. for 21 hours, and the degree of growth of the strain was determined by measuring the optical degree of turbidity of the culture liquor at 660 mμ. Tables 2 and 3 demonstrate the relative degree of growth when the degree of growth observed without the addition of drugs is defined as 100.

TABLE 2

| 1,2,4-Triazole | Relative Degree Of Growth | |
|---|---|---|
| | ATCC 7754 | TRZ-6 |
| 0 g/l | 100 | 100 |
| 1 | 76 | 95 |
| 2.5 | 34 | 70 |
| 5 | 11 | 40 |
| 10 | 11 | 11 |

TABLE 3

| Sodium azide | Relative Degree Of Growth | |
|---|---|---|
| | ATCC 7754 | N-33 |
| 0 mg/l | 100 | 100 |
| 1 | 87 | 95 |
| 2.5 | 42 | 61 |
| 5 | 16 | 30 |
| 10 | 10 | 13 |

As is evident from the results shown in the foregoing Tables 2 and 3, the degree of growth inhibition of drug resistant strains is smaller than that of the parent strain.

As the carbon source in the medium for cultivation, sugars, such as glucose, sucruse, starch hydrolyzate and molasses; organic acids, such as acetic acid and citric acid; alcohols, such as ethanol and methanol; and other assimilable carbon sources can be used. As the nitrogen source, inorganic nitrogenous compounds such as ammonium sulfate, ammonium chloride, ammonium phosphate, ammonium nitrate and urea; and organic nitrogenous substances, such as casaminopeptone and meat extract can be used. In addition, if necessary, phosphate, sulfate, magnesium salt, potassium salt, iron salt, manganese salt, and other inorganic salts may be added. As the growth-promoting substance, organic nutrients, such as yeast extract, malt extract, corn steep liquor, and acid hydrolyzate of soybean cake may be used.

When nutrient requiring strains are employed, the required substances are added to the medium.

Cultivation is carried out aerobically at a temperature of 20°-40° C. and a pH of 3-8.

Recovery of glutathione from yeast cells obtained may be carried out by known methods. For example, cells are harvested by centrifugation, and then glutathione is extracted from the cells with hot water, sulfuric acid, and so forth. Glutathione, thus obtained, is converted into its copper salt by addition of cuprous oxide. Free glutathione is obtained from the copper salt by removing the copper. The glutathione obtained by the present invention was identified by paper chromatography using various developing solvents, infrared spectrum analysis, elementary analysis, amino acid analysis, nuclear magnetic resonance spectrum analysis, and so forth.

Examples will be described below to demonstrate embodiments of the present invention.

EXAMPLE 1

Saccharomyces cerevisiae TRZ-6 is inoculated into a seed culture medium containing 2.5 g/dl (as glucose) molasses, 0.25 g/dl ammonium sulfate and 0.25 g/dl potassium dihydrogen phosphate and cultured with shaking at 30° C. for 24 hours. The seed culture broth is inoculated in an inoculum size of 10% into the following fermentation medium.

Composition of the fermentation medium:

| Molasses (as glucose) | 60 g/l |
|---|---|
| $(NH_4)_2SO_4$ | 10 g/l |
| $NH_4H_2PO_4$ | 2 g/l |
| $K_2SO_4$ | 2.5 g/l |
| $MgSO_4.7H_2O$ | 0.5 g/l |
| $FeSO_4.7H_2O$ | 8 mg/l |
| $MnSO_4.nH_2O$ | 8 mg/l |
| Corn steep liquor | 2.5 g/l |

20 ml of the foregoing fermentation medium is poured into a 250 ml-Erlenmeyer flask and sterilized. After cooling, the seed culture broth is inoculated into the medium and cultured with shaking at 30° C. for 24 hours. After the completion of cultivation, 48.5 g of yeast as dry cells is obtained from 2 l of the fermentation broth by centrifugation. The glutathione content of the dry cells is 3.5%. Glutathione is extracted from the cells with sulfuric acid. Cuprous oxide is added to the extract to afford a copper salt of glutathione. The copper salt is washed with water and suspended in water, and hydrogen sulfide is blown into the suspension to liberate glutathione in the aqueous solution. After removal of sulfuric acid ions, the solution is concentrated under reduced pressure to give 1.20 g of glutathione.

The foregoing procedure is repeated except that the parent strain Saccharomyces cerevisiae ATCC 7754 is employed to afford 54.0 g of yeast as dry cells. The glutathione content of the cells is 0.9%, and 0.29 g of glutathione is obtained from the cells.

EXAMPLE 2

The same procedure as in Example 1 is repeated except that Saccharomyces cerevisiae N-33 is employed to afford 50.3 g of yeast as dry cells. The glutathione content of the dry cells is 2.9%, and 0.99 g of glutathione is obtained from the cells.

EXAMPLE 3

The same procedure as in Example 1 is repeated except that Saccharomyces cerevisiae TRZN-10 is employed to afford 46.7 g of yeast as dry cells. The glutathione content of the dry cells is 3.9%, and 1.32 g of glutathione is obtained from the cells.

What is claimed is:

1. A process for producing glutathione which comprises cultivating a strain selected from the group consisting of Saccharomyces cerevisiae TRZ-6 (FERM BP-194), Saccharomyces cerevisiae N-33 (FERM BP-193) and Saccharomyces cerevisiae TRZN-10 (FERM BP-195) in a culture medium containing assimilable sources of carbon and nitrogen and inorganic salts, accumulating glutathione in the microbial cells, harvesting the cells and recovering the glutathione therefrom.

2. A process according to claim 1, wherein the strain is Saccharomyces cerevisiae TRZ-6 (FERM BP-194).

3. A process according to claim 1, wherein the strain is Saccharomyces cerevisiae N-33 (FERM BP-193).

4. A process according to claim 1, wherein the strain is Saccharomyces cerevisiae TRZN-10 (FERM BP-195).

5. A process according to claim 1, wherein cultivation is carried out at 20°-40° C. and a pH of 3-8.

* * * * *